US011351382B2

(12) United States Patent
Gunderson

(10) Patent No.: US 11,351,382 B2
(45) Date of Patent: Jun. 7, 2022

(54) DETECTING THE ONSET OF SENSING ISSUES USING SHORT INTERVALS

(71) Applicant: Medtronic, Inc., Minneapolis, MN (US)

(72) Inventor: Bruce D. Gunderson, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 87 days.

(21) Appl. No.: 16/904,477

(22) Filed: Jun. 17, 2020

(65) Prior Publication Data

US 2021/0393966 A1  Dec. 23, 2021

(51) Int. Cl.
*A61N 1/37* (2006.01)
*A61B 5/0245* (2006.01)
*A61B 5/11* (2006.01)
*A61N 1/362* (2006.01)
*A61N 1/39* (2006.01)

(52) U.S. Cl.
CPC .............. *A61N 1/37* (2013.01); *A61B 5/0245* (2013.01); *A61B 5/02455* (2013.01); *A61B 5/1116* (2013.01); *A61N 1/3622* (2013.01); *A61N 1/371* (2013.01); *A61N 1/3937* (2013.01); *A61N 1/3956* (2013.01); *A61B 5/1118* (2013.01)

(58) Field of Classification Search
CPC . A61B 5/0245; A61B 5/02455; A61B 5/1116; A61B 5/1118; A61N 1/3622; A61N 1/371; A61N 1/3937; A61N 1/3956
See application file for complete search history.

(56) References Cited

U.S. PATENT DOCUMENTS

| 7,289,851 | B2 | 10/2007 | Gunderson et al. |
| 7,369,893 | B2 | 5/2008 | Gunderson |
| 8,005,539 | B2 | 8/2011 | Burnes et al. |
| 8,078,277 | B2 | 12/2011 | Gunderson et al. |

(Continued)

OTHER PUBLICATIONS

"Lead dysfunction," retrieved from https://www.cardiocases.com/en/pacingdefibrillation/clinical-situation/icd/lead-dysfunction, accessed on Jun. 1, 2020, 5 pp.

(Continued)

*Primary Examiner* — Catherine M Voorhees
(74) *Attorney, Agent, or Firm* — Shumaker & Sieffert, P.A.

(57) ABSTRACT

The disclosure describes an enhancement to lead monitoring techniques, which uses a sensing integrity counter (SIC). The techniques of this disclosure may enhance lead monitoring techniques by detecting possible sensing issues based on a significant increase in periodic, e.g., daily, SIC counts relative to previous periods. Some issues with sensing cardiac signals via implantable cardiac leads can result in an implantable medical device (IMD) measuring very short intervals between what appears to be sensed heart beats. Examples of issues include insulation breach, conductor fracture, or poor electrical connection, which may cause noise that appears to be an R-wave. The IMD may detect the noise, along with actual R-waves, and determine that there are relatively short (e.g., less than a threshold) intervals between the "R-waves." A significant increase in the number or frequency of very short intervals between R-waves may indicate the date/time of a significant sensing issue.

20 Claims, 8 Drawing Sheets

(56) References Cited

U.S. PATENT DOCUMENTS

| | | | |
|---|---|---|---|
| 8,396,543 | B2 | 3/2013 | Hoeppner et al. |
| 8,406,892 | B2 | 3/2013 | Kallis |
| 9,014,807 | B2 * | 4/2015 | Bocek ............... A61N 1/37 607/28 |
| 9,037,240 | B2 | 5/2015 | Gunderson |
| 9,265,951 | B2 | 2/2016 | Sweeney |
| 9,486,155 | B2 | 11/2016 | Sarkar et al. |
| 9,533,165 | B1 | 1/2017 | Gunderson |
| 9,572,990 | B2 | 2/2017 | Gunderson |
| 9,636,506 | B2 | 5/2017 | Gunderson |
| 10,039,919 | B2 | 8/2018 | Kroll et al. |
| 10,188,306 | B2 | 1/2019 | Hierse et al. |
| 10,252,068 | B2 | 4/2019 | Gunderson et al. |
| 10,668,277 | B2 | 6/2020 | Gunderson et al. |
| 2002/0120306 | A1 * | 8/2002 | Zhu ................ A61N 1/36592 607/25 |
| 2008/0161872 | A1 | 7/2008 | Gunderson |
| 2009/0299201 | A1 * | 12/2009 | Gunderson ........ A61N 1/3621 600/508 |
| 2009/0299421 | A1 | 12/2009 | Sawchuk |
| 2010/0023084 | A1 | 1/2010 | Gunderson |
| 2012/0109235 | A1 | 5/2012 | Sheldon et al. |
| 2014/0018873 | A1 | 1/2014 | Gunderson |
| 2015/0005862 | A1 | 1/2015 | Kroll et al. |
| 2015/0088213 | A1 | 3/2015 | Swerdlow |
| 2016/0235992 | A1 | 8/2016 | Sarkar et al. |
| 2016/0375239 | A1 | 12/2016 | Swerdlow |
| 2017/0021166 | A1 | 1/2017 | Bauer et al. |
| 2017/0274204 | A1 | 9/2017 | Gunderson |
| 2017/0296810 | A1 * | 10/2017 | Thakur ................ A61N 1/37 |
| 2018/0161572 | A1 * | 6/2018 | Gunderson ......... A61N 1/056 |
| 2020/0108260 | A1 | 4/2020 | Haddad et al. |

OTHER PUBLICATIONS

"RV Lead Integrity Alert (LIA) Feature," retrieved from https://www.medtronicacademy.com/features/rv-lead-integrity-alert-lia-feature, Apr. 8, 2015, 8 pp.

Ellenbogen et al., "Performance of Lead Integrity Alert to Assist in the Clinical Diagnosis of Implantable Cardioverter Defibrillator Lead Failures Analysis of Different Implantable Cardioverter Defibrillator Leads," Circ Arrhythm Electrophysiol, May 13, 2013, 9 pp.

Gunderson et al., "An Algorithm to Predict Implantable Cardioverter-Defibrillator Lead Failure," Journal of the American College of Cardiology, vol. 44, No. 9, Jul. 2004, 5 pp.

Ng et al., "Incidence of nonphysiologic short VV intervals detected by the sensing integrity counter with integrated bipolar compared with true bipolar leads: clinically inconsequential or cause for concern?," J Interv Card Electrophysiol, Dec. 4, 2013, 5 pp.

Vollmann et al., "Patient Alert™ to detect ICD lead failure: efficacy, limitations, and implications for future algorithms," The European Society of Cardiology, Feb. 12, 2006, 6 pp.

Vollmann et al., "Unusual cause for an increase of the sensing integrity counter in a patient with inappropriate implantable cardioverter-defibrillator therapy," The European Society of Cardiology, Mar. 16, 2007, 3 pp.

Gunderson B D et al., "Causes of ventricular oversensing in implantable cardioverter-defibrillators: Implications for diagnosis of lead fracture," Heart Rhythm, vol. 7, No. 5, May 1, 2010, pp. 626-633.

International Search Report and Written Opinion of International Application No. PCT/US2021/032711, dated Aug. 31, 2021, 10 pp.

Nair Sandeep G et al., "Monitoring for and Diagnosis of Lead Dysfunction," Cardiac Electrophysiology Clinics, vol. 10, No. 4, Nov. 2, 2018, pp. 573-599.

* cited by examiner

DETECTING THE ONSET OF SENSING ISSUES USING SHORT INTERVALS

TECHNICAL FIELD

The disclosure relates medical devices and, more particularly, to a medical device, medical device system and method for detecting the onset of sensing issues.

BACKGROUND

Implantable medical devices (IMDs), including pacemakers and implantable cardioverter-defibrillators (ICDs), sense cardiac electrogram (EGM) signals for identifying cardiac events, e.g., P-waves and R-waves. Episodes of bradycardia, tachycardia and/or fibrillation are detected from the identified cardiac events and responded to as needed with pacing therapy or high-voltage cardioversion/defibrillation therapy. Reliable detection and treatment of potentially life-threatening ventricular tachycardia (VT) and ventricular fibrillation (VF) requires reliable sensing of cardiac signals and identification of cardiac events.

SUMMARY

In general, the disclosure describes an enhancement to lead monitoring techniques, which uses a sensing integrity counter (SIC) that counts very short intervals. The techniques of this disclosure may enhance lead monitoring techniques by detecting possible sensing issues based on a significant increase in periodic, e.g., daily, SIC counts relative to previous periods. Some issues with sensing cardiac signals via implantable cardiac leads can result in an implantable medical device (IMD) measuring very short intervals between what appears to be sensed heart beats, e.g., between sensed R-waves or QRS complexes. Examples of issues include conductor fracture, insulation breach, or poor electrical connection between a lead and the IMD, which may cause noise that appears to be an R-wave. The IMD may detect the noise, along with actual R-waves, and determine that there are relatively short (e.g., less than a threshold) intervals between the "R-waves." A significant, e.g., abrupt, increase in the number or frequency of very short intervals between R-waves may indicate the date/time of the onset of a significant sensing issue.

In one example, the disclosure describes a method comprising: buffering, by processing circuitry of a medical device system comprising a medical device, a predetermined number of sensing integrity counter (SIC) values for the medical device, each of the buffered SIC values determined for a respective period of a plurality of periods preceding a current period; calculating, by the processing circuitry, a measure of central tendency for the buffered SIC values; determining, by the processing circuitry, a trigger threshold based on the calculated measure of central tendency; and triggering a sensing integrity alert in response to determining that an SIC value determined for the current period satisfies the trigger threshold. In other words, the trigger threshold may be dynamically calculated based on the buffered SIC values from the plurality of periods preceding the current period.

In another example, the disclosure describes a medical device system, the system comprising: a medical device; and processing circuitry configured to: buffer a predetermined number of sensing integrity counter (SIC) values for the medical device, each of the buffered SIC values determined for a respective period of a plurality of periods preceding a current period; calculate a measure of central tendency for the buffered SIC values; determine a trigger threshold based on the calculated measure of central tendency; and trigger a sensing integrity alert in response to determining that a SIC value for the current period satisfies the trigger threshold.

In another example, the disclosure is directed to a computer-readable medium containing instructions. The instructions cause a programmable processor to buffer a predetermined number of sensing integrity counter (SIC) values for a medical device, each of the buffered SIC values determined for a respective period of a plurality of periods preceding a current period; calculate a measure of central tendency for the buffered SIC values; determine a trigger threshold based on the calculated measure of central tendency; and in response to determining that a SIC value for the current period satisfies the trigger threshold trigger a sensing integrity alert.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
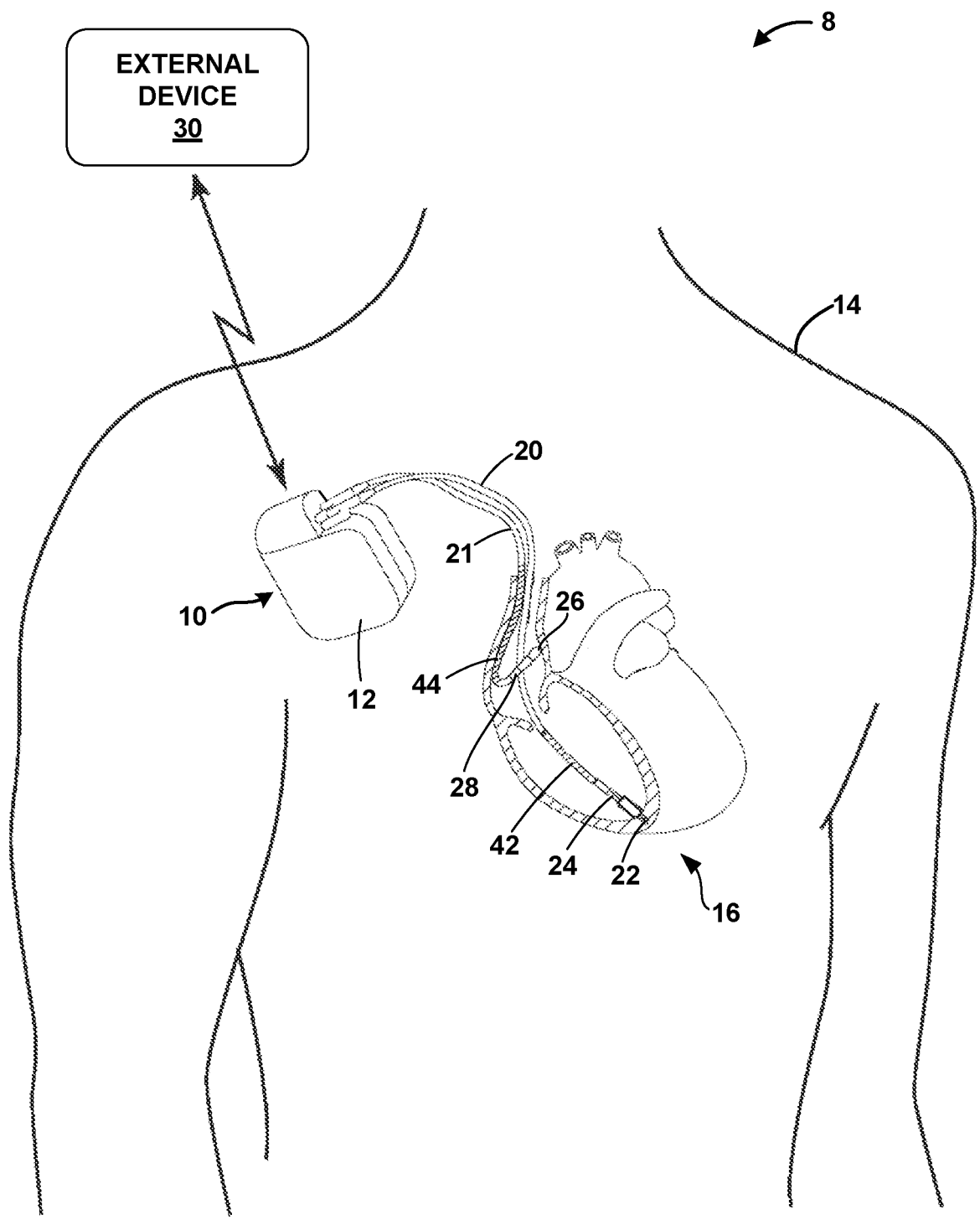
FIG. 1 is an example schematic diagram of an implantable medical device system configured to monitor cardiac function and deliver electrical therapy when needed.

The disclosure describes an enhancement to lead monitoring techniques, which uses a sensing integrity counter (SIC). The techniques of this disclosure may enhance lead monitoring techniques by detecting possible sensing issues based on a significant increase in periodic, e.g., daily, SIC counts relative to previous periods. Some issues with sensing cardiac signals via implantable cardiac leads can result in an implantable medical device (IMD) measuring relatively short intervals between what appears to be sensed heart beats, e.g., between sensed R-waves or QRS complexes. Examples of issues include conductor fracture, insulation breach, or poor electrical connection between a lead and the IMD, which may cause noise that appears to be an R-wave. The IMD may detect the noise, along with actual R-waves, and determine that there are relatively short (e.g., less than a threshold) intervals between the "R-waves." A significant, e.g., abrupt, increase in the number or frequency of short intervals between R-waves may indicate the date/time of a significant sensing issue.

Sensing issues that cause short intervals may eventually lead to misdetection of tachyarrhythmia and delivery of an anti-tachyarrhythmia shock. In this disclosure, processing circuitry of a medical device may receive indications from various sensors and record a variety of "diagnostic events." These diagnostic events may include an abnormal lead impedance, isolated oversensing, a sequence of oversensed events, and inappropriate detection of an abnormal heart rhythm. Sensing issues that generate noise may cause the medical device to deliver a shock to treat an apparent abnormal heart rhythm. The earliest possible alert of a possible sensing issue may give the patient the greatest opportunity to seek medical care before the medical device delivers an inappropriate therapy that might be caused by the device sensing noise, rather than an actual abnormal heart rhythm.

In some lead monitoring techniques, an IMD continually monitors RV pacing lead impedance measurements, the frequency of relatively high rate, non-sustained VT (NSVT) episodes, and the frequency of short ventricular intervals counted on the SIC. According to one such technique, an IMD may identify a potential lead fracture if at least two of the following three criteria are met within the past 60 days:
  Abnormal RV lead impedance (e.g., defined as impedance that is significantly higher or lower than a calculated baseline impedance level);
  Two or more NSVT episodes (e.g., having a threshold number of V-V intervals that are shorter than 220 milliseconds (ms)); or
  At least 30 short V-V interval counts (SIC) within 3 consecutive days.

In some examples, the techniques of this disclosure may provide an advantage over such example techniques in earlier detection of possible sensing issues. In other words, by detecting possible sensing issues early based on a significant increase in daily SIC counts, the techniques of this disclosure may enhance the lead monitoring, provide an earlier warning of potential sensing issues, and allow for medical care before a possible delivery of inappropriate electrical therapy.

The following description may reference illustrative examples. It is understood that in addition to the examples specifically described, other examples may be utilized without departing from the scope of the disclosure. In this disclosure, the terms V-V interval, R-R interval, the interval between sensed heartbeats, the interval between QRS complexes and the interval between R-waves may all be used interchangeably.

FIG. 1 is an example schematic diagram of an implantable medical device system configured to monitor cardiac function and deliver electrical therapy when needed. As illustrated in FIG. 1, a medical device system 8 for sensing cardiac events (e.g., P-waves and R-waves) and detecting tachyarrhythmia episodes may include an implantable medical device (IMD) 10, a ventricular lead 20 and an atrial lead 21. In one example, IMD 10 may be an implantable cardioverter-defibrillator (ICD) capable of delivering electrical therapy such as pacing, cardioversion and defibrillation therapy to the heart 16 of a patient 14. In other examples, IMD 10 may be a pacemaker capable of delivering pacing therapy, including anti-tachycardia pacing (ATP) to the patient, but need not include the capability of delivering cardioversion or defibrillation therapies.

Ventricular lead 20 and atrial lead 21 are electrically coupled to IMD 10 and extend into the patient's heart 16. Ventricular lead 20 includes electrodes 22 and 24 shown positioned on the lead in the patient's right ventricle (RV) for sensing ventricular EGM signals and pacing in the RV. Atrial lead 21 includes tip electrode 26 and ring electrode 28 positioned on the lead in the patient's right atrium (RA) for sensing atrial EGM signals and pacing in the RA. Such a medical device and medical device system is described in commonly assigned U.S. Patent Publication No. 2014/0018873 (hereinafter "the '873 publication") and U.S. Patent Publication No. 2016/0375239, filed on Feb. 2, 2016 by Lambda Nu Technology LLC (hereinafter "the '239 publication"), which are incorporated herein by reference in their entireties.

In the example of FIG. 1, ventricular lead 20 additionally carries a high voltage coil electrode 42, and atrial lead 21 carries a high voltage coil electrode 44, used to deliver cardioversion and defibrillation shock pulses. In other examples, ventricular lead 20 may carry both of high voltage coil electrodes 42 and 44 or may carry another high voltage coil electrode in addition to those illustrated in the example of FIG. 1. Both ventricular lead 20 and atrial lead 21 may be used to acquire cardiac electrogram (EGM) signals from patient 14 and to deliver therapy in response to the acquired data. In this disclosure a cardiac electrogram (EGM) refers to the signal from the lead electrodes of an implanted device. In other examples, an electrocardiogram (ECG) refers to signals from electrodes on the skin surface or subcutaneous electrodes.

Medical device system 8 is shown as a dual chamber ICD including atrial lead 21 and ventricular lead 20, but in some examples, system 8 may be a dual or multi-chamber system including a coronary sinus lead extending into the right atrium, through the coronary sinus and into a cardiac vein to position electrodes along the left ventricle (LV) for sensing LV EGM signals and delivering pacing pulses to the LV. In some examples, system 8 may be a single chamber system, or otherwise not include atrial lead 21.

In some examples, ventricular lead 20 is anchored along the right ventricular apex or the intraventricular septum by a fixation member (not shown), such as tines positioned at the distal end of lead 20 in the vicinity of electrode 22 or a helical screw, which may also serve as electrode 22. Use of a fixation member generally anchors the position of ventricular lead 20 in the RV. However, on rare occasions, ventricular lead 20 may become dislodged from the ventricular myocardium and shift or migrate within the ventricle or toward or within the right atrium, which may cause sensing issues. In other examples, on rare occasions, cracking or other mechanical issues with the lead conductor material or lead insulation may also cause sensing issues. In some examples, patient movement or posture may stretch or bend lead 20 or lead 21, and in examples of a lead with a mechanical issue, the movement, posture, or change in posture may intermittently cause sensing issues such as sensing circuitry of IMD 10 to detect noise. In some examples IMD 10 may interpret the sensed noise as R-waves.

Implantable medical device circuitry configured for performing the methods described herein and an associated battery or batteries are housed within a sealed housing 12. Housing 12 may be conductive and also serve as an electrode for use as an indifferent electrode during pacing or sensing or as an active electrode during defibrillation. As such, housing 12 is also referred to herein as "housing electrode" 12 or "can electrode" 12. In other examples, an indifferent electrode may be separate from housing 12 and placed elsewhere on IMD 10, such as in the header, but perform a function similar to housing electrode 12.

EGM signal data, cardiac rhythm episode data, and lead dislodgement data acquired by IMD 10 can be transmitted to an external device 30. External device 30 may be a computing device, e.g., used in a home, ambulatory, clinic, or hospital setting, to communicate with IMD 10 via wireless telemetry. External device 30 may be coupled to a remote patient monitoring system, such as Carelink®, available from Medtronic Inc., of Minneapolis Minn. External device 30 may be, as examples, a programmer, external monitor, or consumer device, e.g., smart phone.

External device 30 may be used to program commands or operating parameters into IMD 10 for controlling IMD function, e.g., when configured as a programmer for IMD 10. External device 30 may be used to interrogate IMD 10 to retrieve data, including device operational data as well as physiological data accumulated in IMD memory. The interrogation may be automatic, e.g., according to a schedule, or in response to a remote or local user command. Programmers, external monitors, and consumer devices are examples of external devices 30 that may be used to interrogate IMD 10. Examples of communication techniques used by IMD 10 and external device 30 include radiofrequency (RF) telemetry, which may be an RF link established via Bluetooth, WiFi, or medical implant communication service (MICS).

In some examples, the term "near-field" may refer to an EGM recorded by two or more electrodes located in proximity to the source signal for the EGM. For example, a near-field electrogram (NF-EGM) in the ventricle may be recorded from two electrodes, e.g., closely-spaced electrodes near the tip of the lead, positioned on or within the ventricle. At least one of the electrodes may be a small sensing electrode at the tip of the lead. Because these electrodes for a NF-EGM may be closely spaced, their electrical "field of view" may be short-range and dominated by the electrical signals originating in myocardium adjacent to the electrodes, such as the lead tip. The NF-EGM may have advantages for sensing local myocardial electrical activity, and IMDs, such as an ICD or pacemaker, may monitor the NF-EGM continuously to sense cardiac rhythm. As one example, a NF-EGM may be obtained by sensing between tip electrode 22 and coil electrode 44, or between tip electrode 22 and ring electrode 24 of ventricular lead 20.

A far-field electrogram (FF-EGM) may include an EGM recorded by one or more electrodes located at a distance from the source of the EGM. In some examples, a ventricular FF-EGM may record ventricular activation using at least one electrode that is not in a ventricle. In some examples, the ventricular FF-EGM may refer to an EGM recorded between two or more large, widely-spaced electrodes. In some examples, electrodes may be separated by a distance of 10 centimeters (cm) or more. Some examples of widely spaced electrodes may include electrodes used to deliver defibrillation shocks, such as coil electrodes 42 and 44, housing electrode 12, and (in the example dual-coil defibrillation leads), a proximal defibrillation coil and distal defibrillation coil (not shown in FIG. 1). As one specific example, a far-field electrogram (FF-EGM) may be obtained by sensing between coil electrode 42 and housing electrode 12. In some examples a FF-EGM may be referred to as the "shock" EGM recorded between two or among three widely-spaced, large shock electrodes.

The FF-EGM may record a more global signal than the NF-EGM. In some examples, an IMD may analyze a FF-EGM to perform a secondary function that is activated only after analysis of the sensed NF-EGM indicates that VT or VF is present. This secondary function may confirm the presence of VT or VF as indicated by the NF-EGM sensing channel. In some examples, patterns, waveforms, or morphology may be visible on NF-EGM and not on the FF-EGM, and vice versa. The techniques of this disclosure may have advantages in detecting noise and other sensing issues by combining and comparing specific parameters on either or both the near-field and far-field sensing under a variety of conditions.

One or more components of system 8 may identify sensing issues with ventricular lead 20 using the techniques described in this disclosure. For example, IMD 10 may sense a ventricular EGM via ventricular lead 20, e.g., a near-field EGM sensed via tip electrode 22 and ring electrode 24 of ventricular lead 20, or a far-field EGM via housing 12 and high voltage coil electrode 42 (and/or in some cases high voltage coil electrode 44) on the ventricular lead. One or more of IMD 10 and external device 30 may determine whether ventricular lead 20 or atrial lead 21 may develop sensing issues based on the near-field and/or far-field EGM. External device 30 may receive the EGM(s) and/or data representative of the EGM(s) from IMD 10 via RF telemetry.

For example, IMD 10 or external device 30 may identify one or more characteristics of one or both of the near-field and far-field EGM that are associated with the sensing issues of ventricular lead 20. IMD 10 and/or external device 30 may provide an alert in response to detecting sensing issues with ventricular lead 20 or atrial lead 21. In some examples, IMD 10 may alter its sensing or therapy delivery, such as withholding a ventricular defibrillation therapy, in response to detecting sensing issues.

EGM signals may be sensed in real-time and/or recorded in the memory of medical device 10 to be analyzed. In some examples, real-time sensed events may trigger medical device 10 to store a near-field and/or a far-field EGM, e.g., detection of VT or VF may trigger medical device 10 to store one or more EGMs. For example, medical device 10 does not need to store an EGM to measure an RR interval. RR intervals can be determined with real-time sensing using one electrode configuration, such as tip-ring, and also determined from a stored EGM using a different set of electrodes (e.g., RVcoil-Can). The various metrics described herein may likewise be determined based on real-time and/or stored EGMs.

Figure 2:
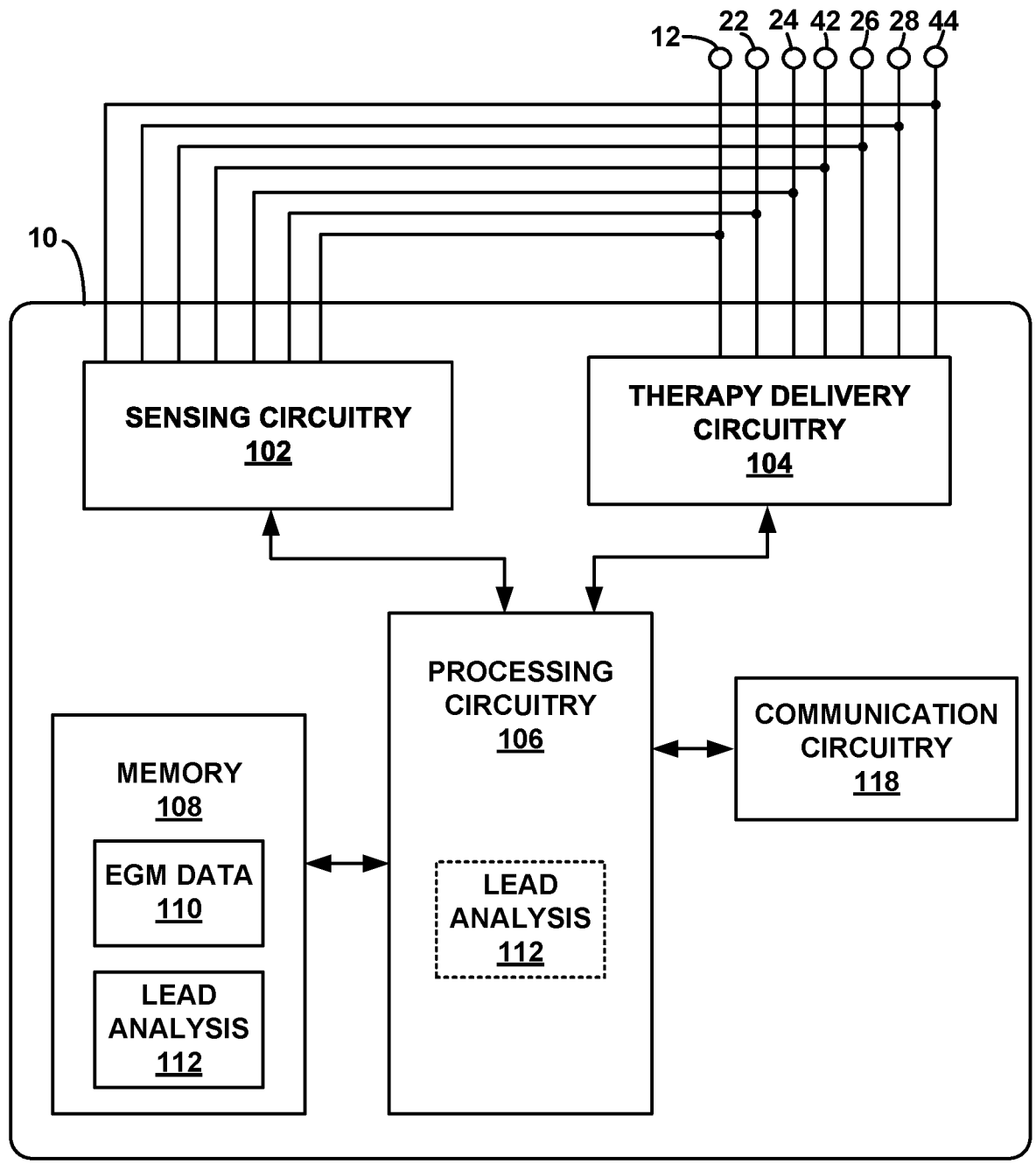
FIG. 2 is a functional block diagram of an example implantable medical device configured to monitor cardiac function and deliver electrical therapy.

FIG. 2 is a functional block diagram of an example implantable medical device configured to monitor cardiac function and deliver electrical stimulation therapy. IMD 10 of FIG. 2 is functional block diagram of an example configuration of IMD 10 described above in relation to FIG. 1. In the example illustrated by FIG. 2, IMD 10 includes sensing circuitry 102, therapy delivery circuitry 104, processing circuitry 106, memory 108, and communication circuitry 118.

Examples of processing circuitry 106 may include may include any one or more of a microcontroller (MCU), e.g. a computer on a single integrated circuit containing a processor core, memory, and programmable input/output peripherals, a microprocessor (µP), e.g. a central processing unit (CPU) on a single integrated circuit (IC), a controller, a digital signal processor (DSP), an application specific integrated circuit (ASIC), a field-programmable gate array (FPGA), a system on chip (SoC) or equivalent discrete or integrated logic circuitry. A processor may be integrated circuitry, i.e., integrated processing circuitry, and that the integrated processing circuitry may be realized as fixed hardware processing circuitry, programmable processing circuitry and/or a combination of both fixed and programmable processing circuitry.

Memory 108 may store program instructions, which may include one or more program modules, which are executable by processing circuitry 106. When executed by processing circuitry 106, such program instructions may cause processing circuitry 106 and IMD 10 to provide the functionality described herein. The program instructions may be embodied in software, firmware and/or RAMware. Memory 108 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Sensing circuitry 102 may be configured to receive cardiac electrical signals from selected combinations of two or more of electrodes 22, 24, 26, 28, 42 and 44 carried by the ventricular lead 20 and atrial lead 21, along with housing electrode 12. In some examples, sensing circuitry 102 is configured to sense cardiac events attendant to the depolarization of myocardial tissue, e.g. P-waves and R-waves. Sensing circuitry 102 may include a switching circuitry for selectively coupling electrodes 12, 22, 24, 26, 28, 42, 44 to sensing circuitry 102 in order to monitor electrical activity of heart 16. In other examples, not shown in FIG. 2, sensing circuitry 102 may receive cardiac electrical signals from other electrodes such as one or more LV electrodes, as described above in relation to FIG. 1. The switching circuitry may include a switch array, switch matrix, multiplexer, or any other type of switching device suitable to selectively couple one or more of the electrodes to sensing circuitry 102. In some examples, processing circuitry 106 selects the electrodes to function as sense electrodes, or the sensing vector, via the switching circuitry within sensing circuitry 102.

Sensing circuitry 102 may include multiple sensing channels, each of which may be selectively coupled to respective combinations of electrodes 12, 22, 24, 26, 28, 42, 44 to detect electrical activity of a particular chamber of heart 16, e.g., an atrial sensing channel and one or more ventricular sensing channels. Each sensing channel may be configured to amplify, filter and rectify the cardiac electrical signal received from selected electrodes coupled to the respective sensing channel to detect cardiac events, e.g., P-waves and/or R-waves. For example, each sensing channel may include one or more filters and amplifiers for filtering and amplifying a signal received from a selected pair of electrodes. The resulting cardiac electrical signal may be passed to cardiac event detection circuitry that detects a cardiac event when the cardiac electrical signal crosses a sensing threshold. The cardiac event detection circuitry may include a rectifier, filter and/or amplifier, a sense amplifier, comparator, and/or analog-to-digital converter.

In some examples, sensing circuitry 102 may include other types of sensors including accelerometers, temperature sensors, pressure sensors, and other sensors. In other examples, sensing circuitry 102 may communicate with other remote sensors implanted in, worn on or placed near patient 14, described above in relation to FIG. 1 (not shown in FIG. 2) via communication circuitry 118. In other examples, other remote sensors may communicate directly with processing circuitry 106 via communication circuitry 118. In some examples the other types of sensors, may provide information such as patient posture, movement, activity and other information.

Sensing circuitry 102 outputs an indication to processing circuitry 106 in response to sensing of a cardiac event, in the respective chamber of heart 16 (e.g., detected P-waves or R-waves). In this manner, processing circuitry 106 may receive detected cardiac event signals corresponding to the occurrence of detected R-waves and P-waves in the respective chambers of heart 16. Indications of detected R-waves and P-waves may be used for detecting ventricular and/or atrial tachyarrhythmia episodes, e.g., ventricular or atrial fibrillation episodes. Sensing circuitry 102 may also pass one or more digitized EGM signals to processing circuitry 106 for analysis, e.g., for use in cardiac rhythm discrimination. Processing circuitry 106 may use the indications of R-waves and/or the digitized ventricular EGM signals to detect diagnostic events and potential sensing issues, according to the techniques described herein. Indications of R-wave and P-wave timing, as well as digitized EGMs, may be stored in memory 108 as EGM data 110.

Memory 108 may also store a lead analysis module 112. Lead analysis module 112 may be a software, firmware, or RAMware module executable by processing circuitry 106 to cause processing circuitry 106 to provide functionality related to identifying sensing issues as described herein. Such functionality may include identifying characteristics of near-field and far-field ventricular EGM signals, detecting sensing issues based on characteristics such as short intervals between diagnostic events, as well as providing an alert, and/or modifying sensing or therapy provided by IMD 10, as described herein. Processing circuitry 106 may load lead analysis module 112 from memory 108 (shown by the dotted lead analysis module 112 within processing circuitry 106) and execute the loaded lead analysis module 112 in response to an event, such as detection of atrial fibrillation via an atrial EGM, or a command from external device 30 received via communication circuitry 118. In other examples, processing circuitry 106 may execute lead analysis module 112 periodically, e.g., according to a schedule, or substantially continuously, throughout the operation of IMD 10.

Processing circuitry 106 may control therapy delivery circuitry 104 to deliver electrical therapy, e.g., cardiac pacing, anti-tachyarrhythmia therapy, or cardioversion or defibrillation shock pulses, to heart 16 (depicted in FIG. 1) according to therapy parameters stored in memory 108. In the example of FIG. 2, therapy delivery circuitry 104 is electrically coupled to electrodes 12, 22, 24, 26, 28, 42, 44, and is configured to generate and deliver electrical therapy to heart 16 via selected combinations of electrodes 12, 22, 24, 26, 28, 42, 44. Electrodes 12, 22, 24, 26, 28, 42, 44 are examples of electrodes 12, 22, 24, 26, 28, 42, 44 described above in relation to FIG. 1. For example, electrode 12 of FIG. 2 corresponds to can electrode 12 depicted in FIG. 1.

Therapy delivery circuit 104 may include charging circuitry, one or more charge storage devices, such as one or more high voltage capacitors and/or one or more low voltage capacitors, and switching circuitry (not shown in FIG. 2) that controls when the capacitor(s) are discharged to selected combinations of electrodes 12, 22, 24, 26, 28, 42, 44. Charging of capacitors to a programmed pulse amplitude and discharging of the capacitors for a programmed pulse width may be performed by therapy delivery circuit 104 according to control signals received from processing circuitry 106.

Memory 108 may be configured to store intervals, counters, or other data used by processing circuitry 106 to control the delivery of pacing pulses by therapy delivery circuitry 104. Such data may include intervals and counters used by processing circuitry 106 to control the delivery of pacing pulses to heart 16. The intervals and/or counters are, in some examples, used by processing circuitry 106 to control the timing of delivery of pacing pulses relative to an intrinsic or paced event in another chamber. Memory 108 also stores intervals for controlling cardiac sensing functions such as blanking intervals and refractory sensing intervals and counters for counting sensed events for detecting cardiac rhythm episodes. Events sensed by sense amplifiers included in sensing circuitry 102 are identified in part based on their occurrence outside a blanking interval and inside or outside of a refractory sensing interval. Events that occur within predetermined interval ranges are counted for detecting cardiac rhythms. According to examples described herein, sensing circuitry 102, therapy circuitry 104, memory 108, and processing circuitry 106 are configured to use timers and counters for measuring sensed event intervals and determining event patterns for use in detecting possible sensing issues, e.g. caused by noise, a fractured conductor and so on.

Processing circuitry 106 may receive analog and/or digitized EGM signals and sensed event signals corresponding to detected R-waves and P-waves from sensing circuitry 102 for use in identifying diagnostic events as well as possible sensing issues when executing lead analysis module 112. As described herein, processing circuitry 106 may detect sensing issues based on an amplitude of the ventricular EGM signal, e.g., an amplitude of R-waves in the digitized ventricular EGM, comparison between near and far field EGM, numbers of short RR intervals and/or variability of RR intervals indicated by the sensing of R-waves and P-waves by sensing circuitry 102.

In some examples, processing circuitry 106 may analyze a near-field and far-field EGM channel to determine R-wave amplitude (RWA), RR variability and other factors. In some examples, processing circuitry 106 may combine other algorithms and techniques with the techniques of this disclosure. For example, in a multiple chamber device, processor 106 may confirm measurements indicating a ventricular lead dislodgement by analyzing cardiac signals on the atrial channel, e.g., as described in the above-incorporated '239 publication.

In more detail, the sensed event intervals, e.g., RR intervals, may be monitored to detect an event interval pattern that is characteristic of sensing issues but distinguishes sensing issues from a tachyarrhythmia event pattern. In some examples, a definition of a short interval, a very short interval, and other classifications may be established and stored in memory 108 and used by processing circuitry 106 to detect periods of time that may include a series of very short intervals. In one example, a short interval may be defined as an interval that is between approximately 120 ms and 250 ms long. The short interval is defined to correspond approximately to an expected P-R interval. The long interval may be defined in ms or as a multiple of the short interval. For example, a long interval may be required to be at least 1.5 times longer than a short interval. A very short interval may be a percentage of either a short or long interval. For example, a very short interval may be defined as less than 120 ms, 60% of a short interval, or some other definition.

The sensing integrity counter records the number of short ventricular intervals that occur. A large number of short ventricular intervals may indicate oversensing. In some examples, processing circuitry 106, may record the number of sensing integrity counts over a predetermined period, e.g., daily, hourly, weekly and so on. For example, processing circuitry 106, or some other processing circuitry described above in relation to FIG. 4, may record a daily, or some other periodic sensing integrity count, which may be referred to as, for example, the daily SIC count.

In some examples, the processing circuitry may execute policies to further discriminate or filter the SIC counts. For example, the processing circuitry may determine that a very short V-V interval, e.g. about 120-130 msec, has occurred within two events of a ventricular pacing event and does not increment the sensing integrity counter. In other words, when a ventricular pacing event is two events prior to the very short interval, e.g. a sequence of VP VS FS, the processing circuitry may not increment the sensing integrity counter. As one example, withholding a sensing integrity count within two events of a pacing event may prevent counting a T-wave oversense followed by an early pre-ventricular contraction, e.g. a sequence of VP TW PVC.

Other specific techniques using the lead integrity alert and sensing integrity counter are described in U.S. Pat. No. 7,369,893 (hereinafter "the '893 patent"), which is incorporated herein by reference in its entirety. In some examples, the techniques of this disclosure may be combined with other arrhythmia discrimination techniques, or lead or sensing integrity issue discrimination techniques, such as those that identify T-wave over-sensing, e.g., as described in the above-incorporated '239 publication.

Processing circuitry 106 may respond to a sudden increase, e.g., significant increase over a relatively short time period, in the sensing integrity count by generating a patient or clinician alert, which may be transmitted by communication circuitry 118. Processing circuitry 106 may additionally respond to a sudden increase in the sensing integrity count by triggering a lead impedance measurement, query other sensors and trigger collection and storage of one or more EGM. In this disclosure, a "relatively short time period" may refer to a time period relative to the useful life of an implantable medical device, for example a time period of a few hours or days.

In some examples, communication circuitry 118 is used to communicate with external device 30, for transmitting data accumulated by IMD 10 and for receiving interrogation and programming commands from external device 30. Under the control of processing circuitry 106, communication circuitry 118 may transmit an alert to notify a clinician and/or the patient that IMD 10 has detected a possible sensing issue with the atrial and/or ventricular leads. This alert enables the clinician to perform additional testing to confirm the issue and to intervene, if necessary, to replace the lead, fix the connection, reposition the lead, or to prevent unnecessary defibrillation therapy from being delivered to the patient. In other embodiments, IMD 10 may be equipped with alert circuitry configured to emit a sensory alert perceptible by the patient, e.g. a vibration or an audible tone, under the control of processing circuitry 106 to alert the patient to the possibility of a possible sensing issue.

Figure 3A:
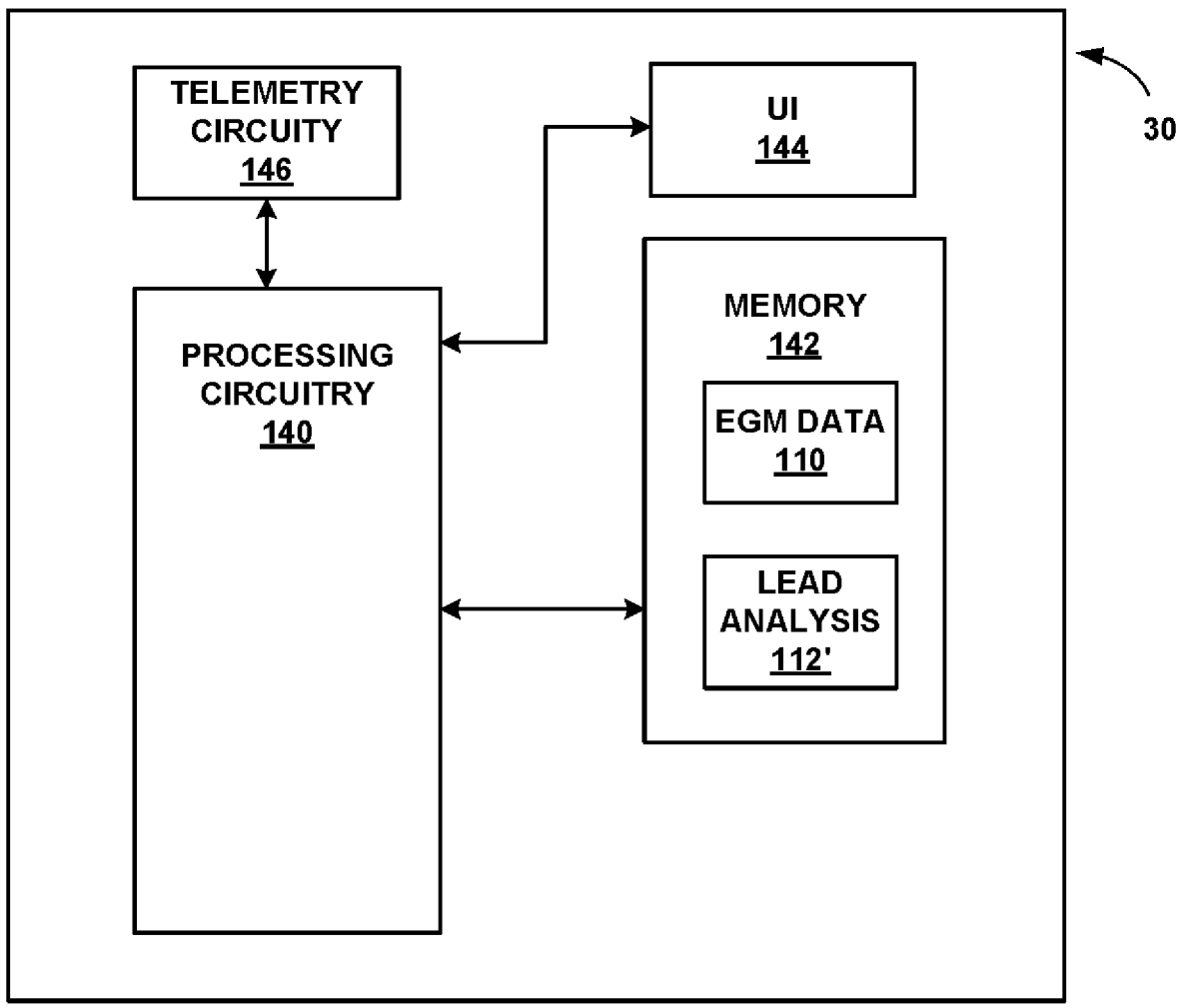
FIG. 3A is a functional block diagram of an example external device configured to communicate with an implantable medical device.
Figure 3B:
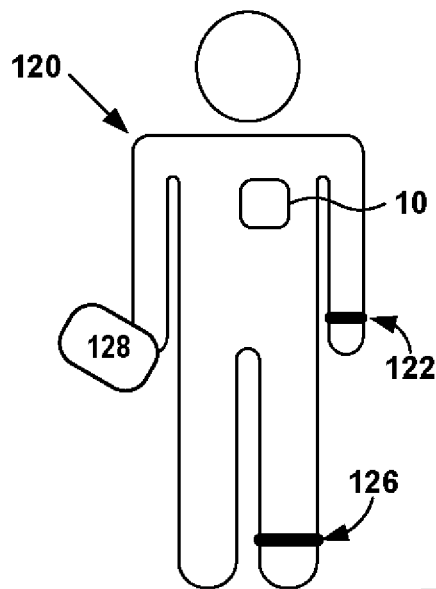
FIG. 3B is a conceptual diagram depicting a patient with an implantable medical device with one or more external devices, including at least one wearable device.

FIG. 3A is a functional block diagram of an external device configured to communicate with an implantable medical device. External device 30 depicted in FIG. 3A is an example of external device 30 described above in relation to FIG. 1. In the example of FIG. 3A, external device 30 includes processing circuitry 140, memory 142, user interface (UI) 144, and telemetry circuitry 146. External device 30 may be a dedicated hardware device with dedicated software for the programming and/or interrogation of IMD 10. Alternatively, external device 30 may be an off-the-shelf computing device, e.g., running an application that enables external device 30 to program and/or interrogate IMD 10. In some examples, external device 30 may be a portable computing device, such as portable device 128 as well as a wearable device, such as devices 122 and 126, depicted in FIG. 3B. In other examples, the functionality ascribed to external device 30 may also be implemented in medical devices worn by or implanted in patient 120 (not shown in FIG. 3B), such as an infusion pump for drug delivery, a leadless pacemaker or other types of medical devices.

In some examples, a user uses external device 30 to select or program values for operational parameters of 1 MB 10, e.g., for cardiac sensing and therapy delivery. In some examples, a user may use external device 30 to receive data collected by IMD 10, such as cardiac EGM data 110 or other operational and performance data of IMD 10. The user may also receive one or more alerts provided by IMD 10, or data regarding modifications to sensing or therapy made by 1 MB 10 in response to detecting sensing issues, e.g., a trend in daily sensing integrity indicator counts, lead impedance measurements and other information. The user may interact with external device 30 via UI 144, which may include a display to present a graphical user interface to a user, and a keypad or another mechanism for receiving input from a user. External device 30 may communicate wirelessly with IMD 10 using telemetry circuitry 146, which may be configured for RF communication, including inductive communication, with communication circuitry 118 of IMD 10.

Processing circuitry 140 may include any combination of integrated circuitry, discrete logic circuitry, analog circuitry, such as one or more microprocessors, DSPs, ASICs, or FPGAs. As described above in relation to processing circuitry 106 in FIG. 2, in some examples, processing circuitry 140 may include multiple components, such as any combination of one or more microprocessors, one or more DSPs, one or more ASICs, or one or more FPGAs, as well as other discrete or integrated logic circuitry, and/or analog circuitry. In some examples, processing circuitry 140 may be configured with more processing power than the processing power available to processing circuitry 106. Processing circuitry 140 may be configured to perform more complex calculations and analysis functions than performed by the processing circuitry in the medical device.

As with memory 108, described above in relation to FIG. 2, memory 142 may store program instructions, which may include one or more program modules and are executable by processing circuitry 140. When executed by processing circuitry 140, such program instructions may cause processing circuitry 140 and external device 30 to provide the functionality described herein. The program instructions may be embodied in software, firmware and/or RAMware. Memory 142 may include any volatile, non-volatile, magnetic, optical, or electrical media, such as a RAM, ROM, NVRAM, EEPROM, flash memory, or any other digital media.

In some examples, processing circuitry 140 of external device 30 may be configured to provide some or all of the functionality ascribed to processing circuitry 106 of IMD 10 herein. For example, processing circuitry 140 may receive EGM data 110, e.g., of one or more ventricular EGM signal sensed via ventricular lead 20 from IMD 10 via telemetry circuitry 146, and may store the EGM data 110 in memory 142. EGM data 110 may be current EGM data, or data previously collected and stored by IMD 10. Using EGM data 110, processing circuitry 140 of external device 30 may identify characteristics of the atrial and ventricular EGM(s) indicative of possible sensing issues with the atrial and/or ventricular lead, including sensed noise, lead impedance trends and so on. Based on the detection of possible sensing issues, or other diagnostic events, processing circuitry 140 may provide an alert to a user, e.g., via UI 144. In some examples, lead analysis module 112' may provide the functionality for the detection of possible sensing issues. In some examples lead analysis module 112' may be a software module stored in memory 142, and loaded and executed by processing circuitry 140 (as illustrated by the dotted outline lead analysis module 112' within processing circuitry 140), e.g., in response to a command from the user, or based on detection criteria implemented by processing circuitry 140.

Figure 4:
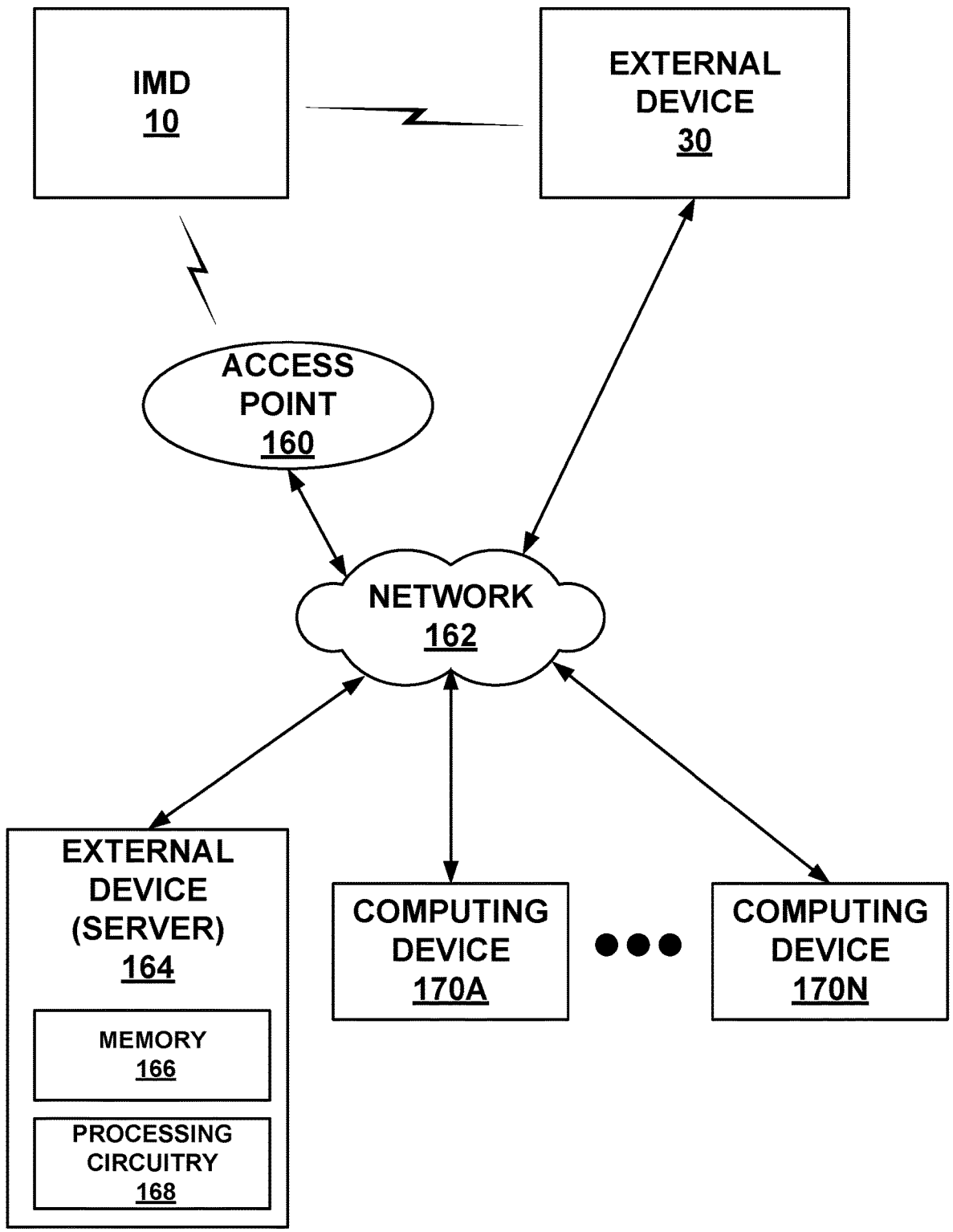
FIG. 4 is a functional block diagram illustrating an example system that includes external computing devices, such as a server and one or more other computing devices, that are coupled to the IMD and programmer shown in FIG. 1 via a network.

FIG. 4 is a functional block diagram illustrating an example system that includes external computing devices, such as a server 164 and one or more other computing devices 170A-170N, that are coupled to IMD 10 and external device 30 via a network 162. IMD 10 and external device 30 are examples of IMD 10 and external device 30 described above in relation to FIGS. 1-3.

In this example, IMD 10 may use its communications module 118 to, e.g., at different times and/or in different locations or settings, communicate with external device 30 via a first wireless connection, and to communication with an access point 160 via a second wireless connection. In the example of FIG. 4, access point 160, external device 30, server 164, and computing devices 170A-170N are interconnected, and able to communicate with each other, through network 162.

Access point 160 may comprise a device that connects to network 162 via any of a variety of connections, such as telephone dial-up, digital subscriber line (DSL), or cable modem connections. In other examples, access point 160 may be coupled to network 162 through different forms of connections, including wired or wireless connections. In some examples, access point 160 may be co-located with patient 14 (shown in FIG. 1). Access point 160 may interrogate IMD 10, e.g., periodically or in response to a command from patient 14 or network 162, to retrieve EGM data 110 or other operational data from IMD 10. Access point 160 may provide the retrieved data to server 164 via network 162.

In some cases, server 164 may be configured to provide a secure storage site for data that has been collected from IMD 10 and/or external device 30, such as the Internet. In some cases, server 164 may assemble data in web pages or other documents for viewing by trained professionals, such as clinicians, via computing devices 170A-170N. The illustrated system of FIG. 4 may be implemented, in some aspects, with general network technology and functionality similar to that provided by the Medtronic CareLink® Network developed by Medtronic Inc. of Minneapolis Minn.

In some examples, one or more of access point 160, server 164, or computing devices 170 may be configured to perform, e.g., may include processing circuitry configured to perform, some or all of the techniques described herein relating to detecting dislodgment of a ventricular lead detecting a sensing or lead integrity issue. In the example of FIG. 4, server 164 includes a memory 166 to store EGM data received from IMD 10, and processing circuitry 168, which may be configured to provide some or all of the functionality ascribed to processing circuitry 106 of IMD 10 herein. For example, processing circuitry 168 may identify characteristics of the one or more ventricular EGMs indicating sensing issues based on the EGM data received from IMD 10. Processing circuitry 168 may also identify sensing issues based on identified characteristics of the EGM data, as well as based on an abrupt increase in sensing integrity counts, changes in lead impedance and other indications. Processing circuitry 168 may provide an alert to a user, e.g., via external device 30 or one of computing devices 170. As described above in relation to FIG. 3A, the processing circuitry of computing devices 170A-170N and of server 164 may be configured to perform more complex calculations and functions than performed by other processing circuitry depicted in FIG. 4.

In the example of FIGS. 1-4, any of memory 108, 142, and 166 may be considered operatively coupled to any of the processing circuitry of the system described by FIG. 4. In some examples, memory may be operatively coupled to processing circuitry such as via a leadframe, circuit paths, a circuit bus, and so on. For example, memory 108 may be operatively coupled to processing circuitry 106 by a circuit bus. Memory 142 in FIG. 3A and memory 166 of FIG. 4 may also be operatively coupled to processing circuitry 106, or other processing circuitry via communication links, as described above.

Figure 5:
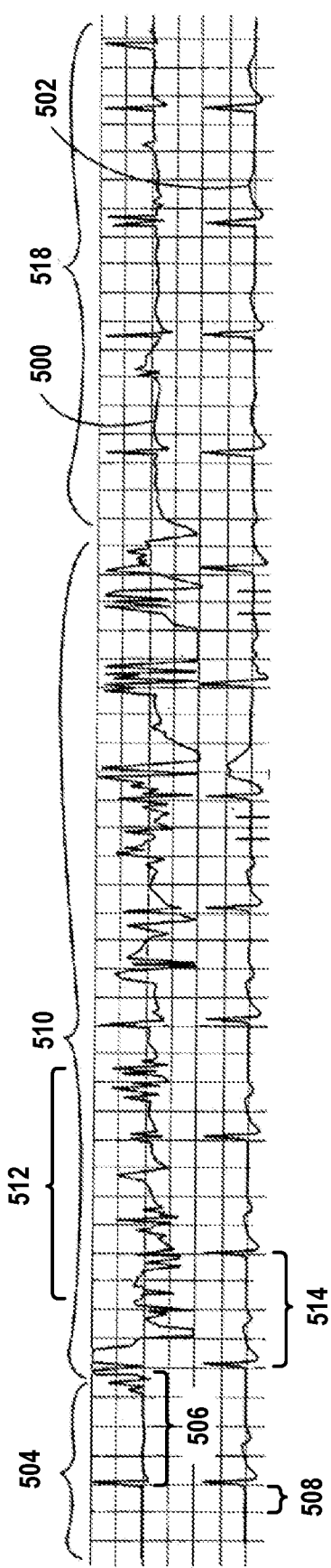
FIG. 5 is a portion of stored cardiac electrograms, including a near-field electrogram and a far-field electrogram, where there is an indication of short intervals between R-waves.

FIG. 5 is a portion of a stored electrogram showing near-field on the top with a noisy signal and far-field pulses where the noise on the near-field would likely cause an indication of what may appear to be short R-R intervals. The description of FIG. 5 may refer to components described above in relation to FIGS. 1, 2 and 3A. In the example of FIG. 5, the near-field signal 500 is recorded between the tip and ring electrodes of the bipolar sensing lead, such as electrodes 24 and 22, described above in relation to FIG. 1. The near-field signal may be input to a sense amplifier that senses voltages that exceed a threshold. The far-field signal 502 in the example of FIG. 13, may be recorded between one or more secondary electrodes such as the lead coils 40 or 42 and the can electrode 12 or a sensing lead in another part of the heart (left atrium or right ventricle) described above in relation to FIG. 1. Processing circuitry, such as processing circuitry 106, may label each sensed event from the near-field signal, with a label such as Fibrillation Sense (FS), Fibrillation Detected (FD), Tachycardia Sensed (TS) Ventricular Sense (VS) Capacitors charged (CE), or Capacitor Discharged (CD) and store the labels along with the electrograms at memory 108. The labels may depend on the interval between each sensed event. For example, on the left of the curve of electrogram 504 is a relatively normal R-wave representation in period 504. The period 506 between the events is approximately 670 milliseconds (ms). Note each division 508 in FIG. 5 is a 200 ms division.

The period of relative normal R-wave representation 504 is followed by a series of erratic signals 510 that indicate a possible oversensing issue such as noise caused by, for example a fractured lead conductor or insulation break on a lead, such as in ventricular lead 20 or atrial lead 21 described above in relation to FIG. 1. The interval between the events in the erratic period 510, for example the apparent R-R intervals, or events, in period 512, may be very short, e.g. 130 ms or 120 ms. IMD 10 may label such very short intervals as a sensed fibrillation. If the very short intervals during period 510 meet the criteria for the sensing integrity counter, as described in detail in the '893 patent, the sensing integrity counter may increment the sensing integrity count.

In some examples, because oversensing may be caused by a lead related problem and may be near the blanking period of the sense amplifier, the sensing integrity counter may quantify this oversensing by counting the number of RR-intervals that are determined to be less than a predetermined time period above the blanking period. In some examples the predetermined time period may be set to a value such as 20 ms above the blanking period. In some examples, the blanking period for an IMD, such as IMD 10, may be programmed to a value such as 120 ms, the predetermined threshold for the sensing integrity counter may therefore be equal to approximately 140 ms. In some examples, the blanking period is programmable and can therefore have a value other than 120 ms, the predetermined threshold may be simply set equal to the programmed blanking period plus a time values such as 20 ms, with a predetermined maximum value, such as of 170 ms. While in this example, the predetermined time period for the sensing integrity counter is described as being 20 ms, it is understood that using any other time period may also be used.

An examination of far-field signal 502, however, shows a relatively regular far-field R-wave during the period of erratic signals 510. For example, the R-R interval 514 is approximately 670 ms, as also shown during period 504. Also, during the period of relative normal R-wave representation 504, the far-field signal 502 follows the near-field signal 500 quite closely. When the near-field signal 500 becomes erratic during period 510, far-field signal 502 continues to show regular R-wave far-field pulses indicating that the erratic portion 510 may cause oversensing. During the period labeled as 518, the near-field signal 500 appears to recover to a period of relative normal R-wave representation, and the far-field signal 502 continues to follow the near-field signal 500, suggesting that the irregular portion 510 of the near-field signal 500 may be caused by a lead issue resulting in oversensing. In some examples, the erratic signals during period 510 may be caused by a failure with intermittent erratic signals, since the R-wave pulses of near-field signal 500 recovered at a period of relative normal R-wave representation 518.

Therefore, as described above in relation to FIG. 2, IMD 10 may trigger an alert should the sensing integrity counter increment above the dynamically calculated threshold value. In other words, rather than a fixed threshold, the sensing integrity count threshold may be dynamically calculated based on a number of previous periodic, e.g. daily, SIC counts. In some examples, IMD 10 may also trigger a lead impedance measurement, or some other confirmation test, as soon as the sensing integrity counter exceeds the threshold, rather than waiting for a daily or some other periodic lead impedance measurement. In other words, determining that a SIC value determined for the current period satisfies the trigger threshold may include determining that the SIC value determined for the current period satisfies the trigger threshold prior to an end of the current period. By triggering a lead impedance measurement as soon as possible after the sensing integrity counter exceeds the threshold, IMD 10 may provide an advantage of taking a lead impedance measurement during the period of an intermittent sensing issue, e.g. during period 510. Waiting to trigger the lead impedance measurement may cause IMD 10 to take the measurement after the noise period has ended, e.g. during period 518, which may result in a normal lead impedance measurement. As described above in relation to FIG. 1, an intermittent lead integrity issue may be caused by patient position, posture, movement, in the presence of a noise source, or some other intermittent root cause.

As discussed in the '893 patent, with a pattern of this nature, it may be premature to deliver electrical stimulation therapy to the patient, particularly a painful defibrillation shock, in response to erratic portion 510 sensed in near-field signal 500. In some examples, a variety of techniques may be used to avoid delivering a shock under these conditions. First, if there is a detection of an irregularity as seen in the erratic portion 510 of near-field signal 500, an 1 MB, such as IMD 10 described above in relation to FIG. 1 may wait to see whether the problem goes away by increasing the number of intervals for detection as described above in relation to FIG. 5. Should the problem go away, the very short intervals between what appears to be sensed heart beats may be caused by an oversensing problem and not an arrhythmia. Also, IMD 10 may be configured to change sensing lead electrode configuration. In other words, 1 MB 10 may include programming to automatically change the sensing lead configuration, e.g. from bipolar to unipolar sensing. Finally, 1 MB 10 may output an alert, such as a vibration, audio alert, or a signal output to external device 30, described above in relation to FIGS. 1 and 3, to advise the patient to see a doctor to have the ICD and its leads checked.

Figure 6:
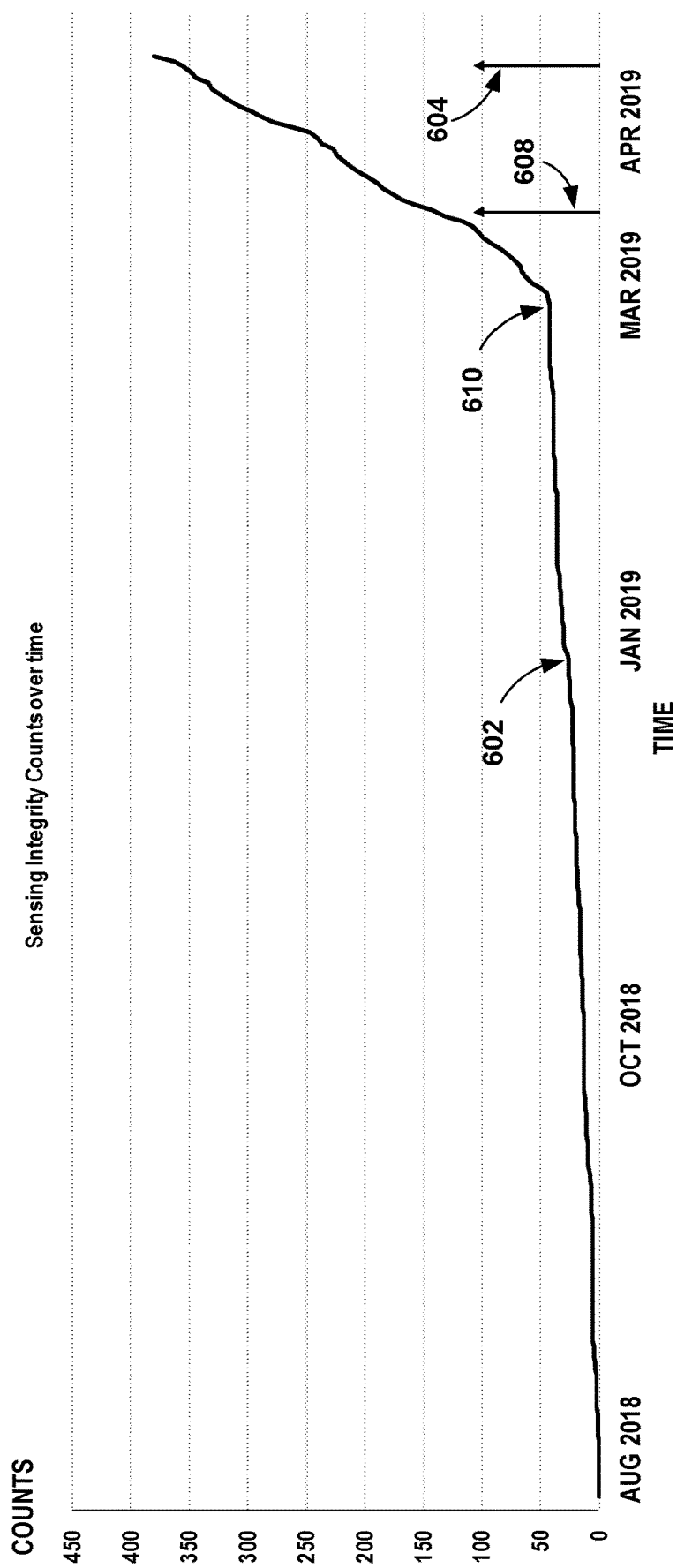
FIG. 6 is a time graph illustrating sensing integrity counts over a period of time.

FIG. 6 is a time graph illustrating sensing integrity counts over an extended period of time. The periodic, e.g., daily, weekly, hourly and so on, sensing integrity counts 602 illustrated in FIG. 6 may be stored, for example, at memory 108 by processing circuitry 106 as described above in relation to FIG. 2. The daily sensing integrity counts 602 may also be transmitted to one or more external devices as described above in relation to FIGS. 1, 3 and 4.

In the example of FIG. 6, a medical device, such as IMD 10 described above in relation to FIGS. 1 and 2, recorded a steady increase in sensing integrity counts 602 beginning in August 2018. In mid-March of 2019, the medical device logged a non-sustained tachycardia diagnostic event 608. In mid-April 2019, the medical device logged a lead integrity alert 604 as well as a low lead impedance. Upon further investigation, the root cause of the lead integrity sensing issue was a tip to ring insulation breach in the lead. An example of tip electrode 22 and ring electrode 24 for ventricular lead 20 is depicted in FIG. 1. Similarly, FIG. 1 depicts atrial lead 21, which includes tip electrode 26 and ring electrode 28 positioned on the lead in the patient's right atrium.

FIG. 6 also indicates a significant increase over a relatively short time period, e.g. abrupt increase, in SIC counts 610 in early March of 2019. The example of FIG. 6 indicates that by detecting possible sensing issues early based on an abrupt increase in periodic SIC counts 610, the techniques of this disclosure may enhance the lead monitoring techniques and provide an earlier warning of potential sensing issues, such as an insulation breach. The early warning may allow for medical care before a possible delivery of inappropriate electrical stimulation therapy.

Figure 7:
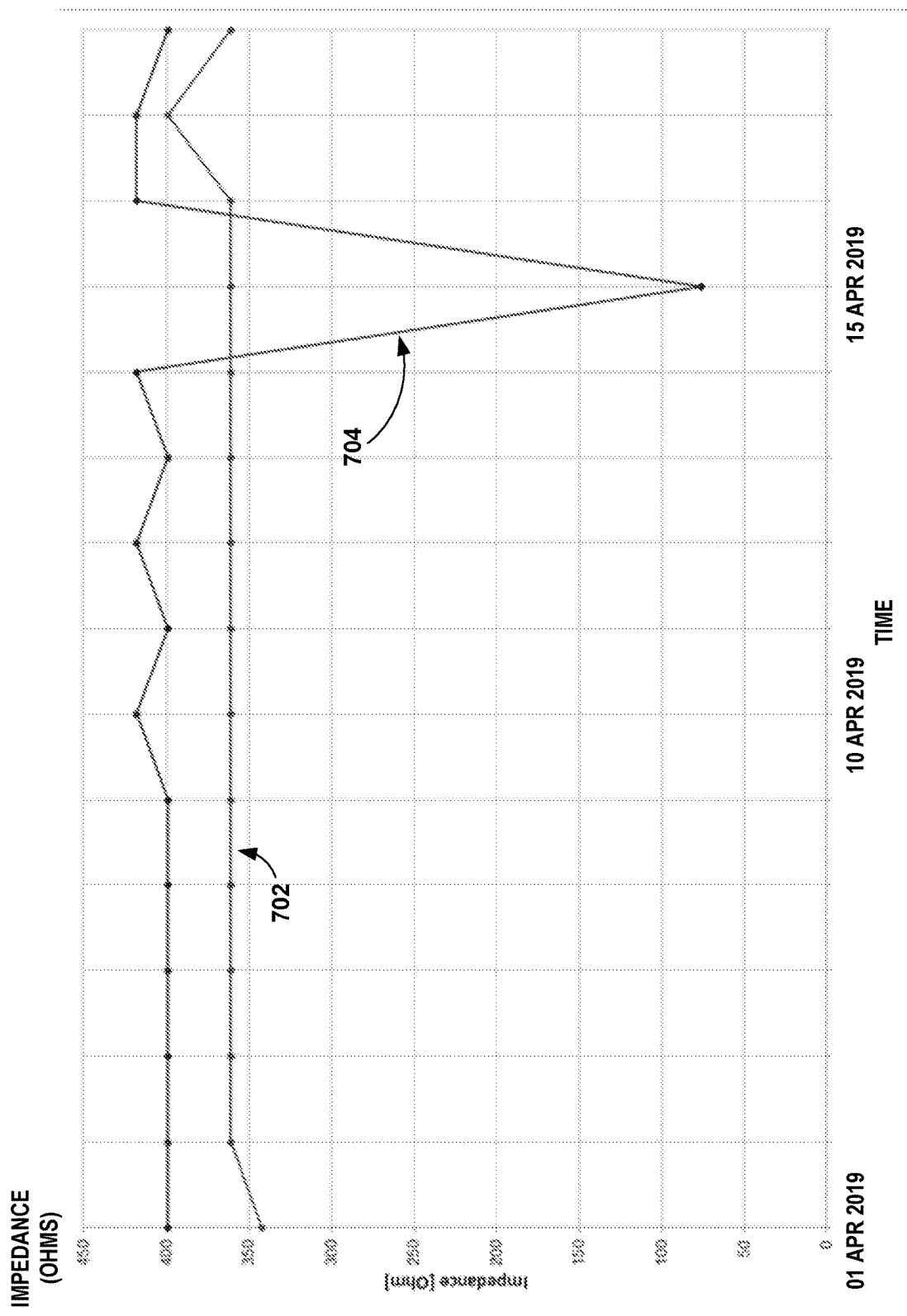
FIG. 7 is a time graph illustrating lead impedance measurements over a period of time included in the time graph of FIG. 6.

FIG. 7 is a time graph illustrating lead impedance measurements that corresponds to a time period as shown in the time graph of FIG. 6. The example of FIG. 7 depicts a trend of daily atrial lead impedance measurements 702 and ventricular lead impedance measurements 704. The ventricular lead impedance measurement 704 for 15 Apr. 2019 shows a one-day drop in lead impedance, which returns to normal by the next day. As described above in relation to FIG. 1, sensing issues caused by some lead weaknesses may be intermittent. In some examples, changes in patient posture, activity and other short-term changes may exacerbate a weakness in lead insulation, conductor, connection and so on. As described above in relation to FIGS. 2 and 5, a medical device, such as IMD 10, may trigger other measurements based on a sudden increase in sensing integrity counts. In some examples, the medical device may trigger a lead impedance measurement without waiting for the daily lead impedance measurement. In this manner, the techniques of this disclosure may collect additional diagnostic information to help track down a possible intermittent sensing issue.

Figure 8:
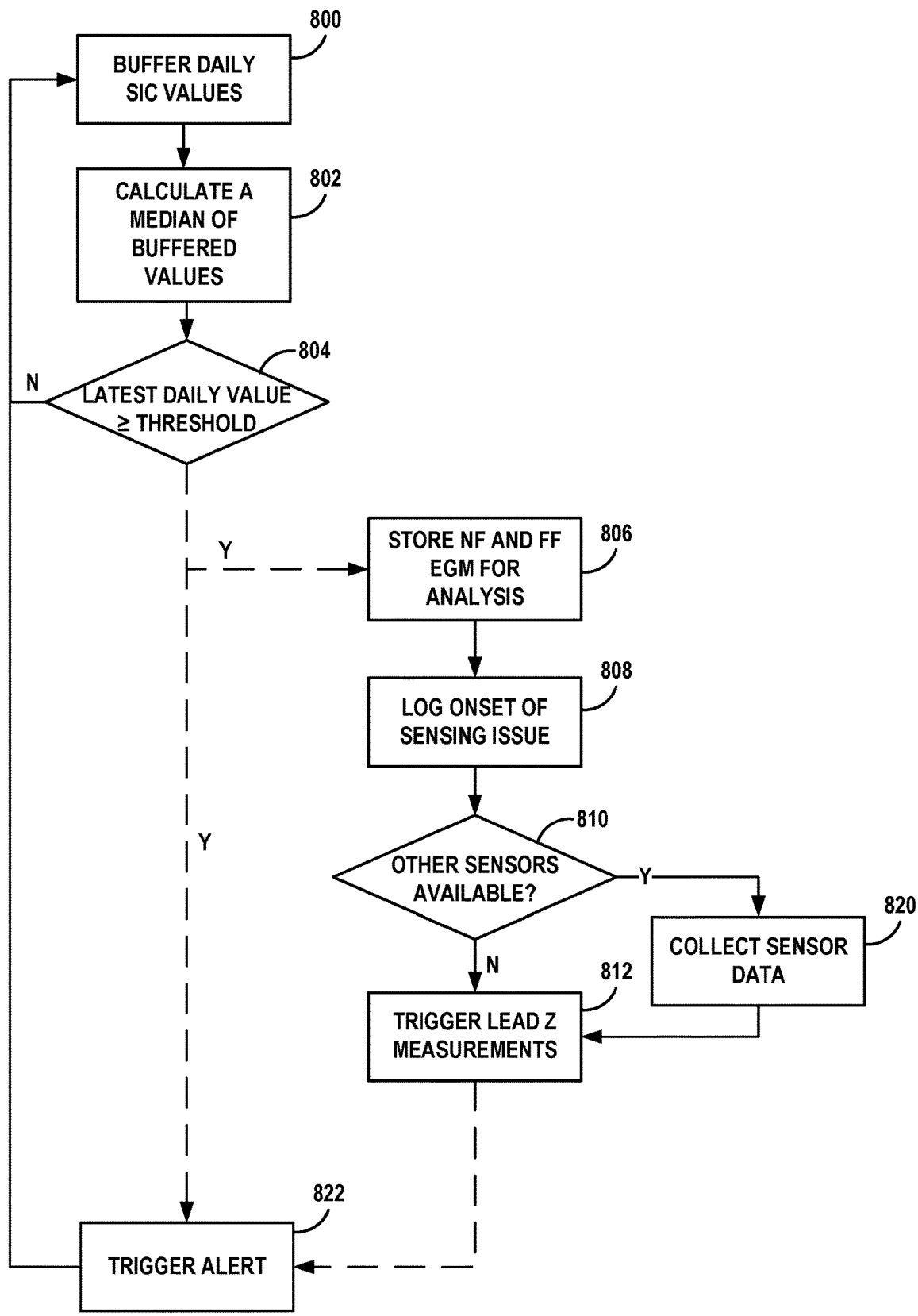
FIG. 8 is a flowchart illustrating an example operation of the system of this disclosure.

FIG. 8 is a flowchart illustrating an example operation of the system of this disclosure. The blocks of FIG. 8 will be described in terms of the devices described FIGS. 1, 2, 3A and 3B, unless otherwise noted. However, in some examples, the example operation of FIG. 8 may be performed, in whole or part, but one or more other devices, such as those described with respect to FIG. 4.

Processing circuitry 106 may buffer a predetermined number of daily (or other periodic) SIC values, such as the daily sensing integrity counts 602 described above in relation to FIG. 5 (800). In other words, processing circuitry of IMD 10 may store a specified number of daily SIC values in a buffer, which may be stored at memory 108. In some examples the buffered daily SIC values may be uploaded to an external device, as described above in relation to FIGS. 3A, 3B and 4. The specified number of daily SIC values may be for example, a rolling two week buffer, a ten-day buffer, a thirteen-day buffer or some other specified number of daily SIC values. The specified number of daily SIC values may be values for N consecutive periods that precede the current period, including the most recently preceding period.

After buffering the SIC values, processing circuitry may perform one or more calculations based on the buffered SIC values. To simplify the description, the steps of FIG. 8 will focus on calculating a median of the buffered values (802). However, in other examples, the processing circuitry may calculate any measure of the buffered values. For example, the processing circuitry may calculate any one or more measures of central tendency, such as an average, mode, as well as the median. In other examples, processing circuitry may calculate a measure of distribution of the buffered daily SIC values, such as standard deviation, skewness or some other calculation. In other examples, the processing circuitry may calculate other measures based on statistical process control (SPC) techniques. Some examples of SPC may include a combination of one or more measures of central tendency and a variation of the baseline to determine the location of an outlier value. Some examples of SPC may also include upper control limits, lower control limits, histograms, scatter plots and so on to determine when a value is an outlier value. In some examples, as described above in FIGS. 3A and 4, more complex calculations may be offloaded to an external computing device. The one or more calculations may also be stored at a memory location such as memory 108, or a memory on an external device.

Processing circuitry 106 may compare the latest daily sensing integrity count value to a threshold value determined based on the median, or other measure, of buffered values (804). The threshold value may be considered adaptive since it varies over time based on the buffered SIC values. Based on the comparison, the processing circuitry may determine whether the latest daily sensing integrity count value indicates a sudden increase in sensing integrity counts.

In the illustrated example, processing circuitry 106 determines that the latest daily sensing integrity count value satisfies the threshold (YES branch of 804) based on daily value being greater than or equal to the threshold, and that the latest daily sensing integrity count value does not satisfy the threshold (NO branch of 804) based on value being less than the threshold. In other examples, "satisfies a threshold" includes being greater than a threshold or less than a threshold. According to the example of FIG. 8, processing circuitry 106 may continue to buffer the daily SIC values (800), calculate the median (802), and determine the next daily SIC value based on current latest daily SIC value not satisfying the threshold (NO branch of 804).

In this disclosure, the predetermined threshold value may also be referred to as a trigger threshold. In other words the predetermined threshold may be a trigger threshold to detect a sudden increase in daily SIC values. In some examples, the trigger threshold value may be based on the calculated median, or other calculation. For example, the trigger threshold may be set as a percentage increase greater than the median value. In some examples, the threshold may be set as a twenty percent increase over the median value. In other examples, the threshold may be set to a fixed constant value greater than the median, such as four counts over the median. In other words, when the latest daily sensing integrity count exceeds the threshold (latest SIC count≥median+4), the processing circuitry may determine that there has been a sudden increase in the sensing integrity counts. In other examples, the threshold may be set to a percentage change (e.g. an increase or a decrease) from the measure of central tendency, for example a percent increase greater than the calculated median. In other examples, the threshold may be based on a slope change, or a derivative change in the sensing integrity count curve 602 described above in relation to FIG. 6.

In some examples, based on the latest daily SIC count satisfying the threshold (YES branch of 804), the processing circuitry on either IMD 10 or an external device may trigger an alert (822) and continue to monitor diagnostic events from the patient. In other examples, when processing circuitry 106 determines that there has been a sudden increase in the sensing integrity counts, the processing circuitry may trigger one or more confirmation tests. In some examples, a confirmation test may include triggering one or more EGMs to be stored for analysis (806). In some examples the processing circuitry may collect and store either or both of a near field and a far field EGM.

The processing circuitry may log the onset of a sensing issue (808) and store the time of onset at a memory location and may store one or more EGM segments including the time of onset. In some examples, processing circuitry 106 may determine whether other sensors are available (810), which may help troubleshoot a possible lead sensing issue. In some examples, the location of the patient may be subject to external noise, such as near machinery, electronic equipment, RF transmitting systems and so on. In some examples, the patient activity or posture may impact noise sensed by IMD 10. As described above in relation to FIG. 2, IMD 10 may include other sensors such as accelerometers, temperature sensors and other sensors. In other examples, one or more external devices may include sensors that could provide information. In some examples, a wearable or portable device may include circuitry to determine a geographic location, such as by using global position system (GPS), WiFi or BLUETOOTH transmissions. In this disclosure, a geographic location indicates a position such as a street address, a location in relation to one or more other geographic objects, such as one or more buildings or landmarks or some similar geographic position. A geographic location may provide information about the location of the patient and/or the medical device in relation to a source of noise, such as a large magnetic field, industrial motors, other medical equipment, and so on.

In some examples, a wearable or portable device may include accelerometers and other sensors to determine patient activity, such as a fitness tracker device. If other sensors are available (YES branch of 810), the processing circuitry may collect sensor data 820, such as patient location, activity, temperature, and so on.

In some examples, processing circuitry 106 may also trigger a lead impedance measurement test, a.k.a. a lead Z measurement (812), whether or not there are other sensors available (NO branch of 810). As described above, in some examples, processing circuitry 106 and/or processing circuitry 140 of external device 30 may trigger an alert (822) to notify the patient, or medical professional, that there may be a sensing issue. As described above in relation to FIG. 2, in some examples the alert may be audible or vibration. As described above in relation to FIG. 3, in some examples the alert may display on the user interface, e.g. UI 144 of an external device. As described above in relation to FIG. 4, in some examples, the alert may be transmitted over a network.

Processing circuitry 106, or other processing circuitry of the medical device system, may determine the current, latest, or most-recent sensing integrity count value for the day or other period at the end of the day or other period, and compare the determined value to the threshold at that time. In other examples, as processing circuitry 106 increments the sensing integrity count value during the day or other period, the processing circuitry may compare the incremented value to the threshold. In this manner, processing circuitry 106 may more quickly and effectively identify the time of onset of a sensing integrity issue which may occur during a given day or other evaluation period.

In one or more examples, the functions described above may be implemented in hardware, software, firmware, or any combination thereof. For example, the various components of FIGS. 2 and 3, such as processing circuitry 106, processing circuitry 140, and telemetry circuitry 146 may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

The term "non-transitory" may indicate that the storage medium is not embodied in a carrier wave or a propagated signal. In certain examples, a non-transitory storage medium may store data that can, over time, change (e.g., in RAM or cache).

By way of example, and not limitation, such computer-readable storage media, such as memory 142 and memory 108, may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer readable media. In some examples, an article of manufacture may include one or more computer-readable storage media.

Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Combinations of the above should also be included within the scope of computer-readable media.

Instructions may be executed by one or more processors, such as one or more DSPs, general purpose microprocessors, ASICs, FPGAs, or other equivalent integrated or discrete logic circuitry. Accordingly, the term "processor," and "processing circuitry" as used herein, such as ECS controller 202, may refer to any of the foregoing structure or any other structure suitable for implementation of the techniques described herein. Also, the techniques could be fully implemented in one or more circuits or logic elements.

The techniques of this disclosure may be implemented in a wide variety of devices or apparatuses, including, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

These and other aspects are within the scope of the following examples and the claims.

The following examples illustrate methods, devices, and systems described herein.

Example 1. A method comprising: buffering, by processing circuitry of a medical device system comprising a medical device, a predetermined number of sensing integrity counter (SIC) values for the medical device, each of the buffered SIC values determined for a respective period of a plurality of periods preceding a current period; calculating, by the processing circuitry, a measure of central tendency for the buffered SIC values; determining, by the processing circuitry, a trigger threshold based on the calculated measure of central tendency; and triggering a sensing integrity alert in response to determining that an SIC value determined for the current period satisfies the trigger threshold.

Example 2. The method of example 1, wherein the measure of central tendency comprises any one of an average, a mode, or a median of the buffered SIC values.

Example 3. The method of any combination of examples 1-2, wherein the predetermined number of SIC values is thirteen.

Example 4. The method of any combination of examples 1-3, further comprising triggering a confirmation test in response to determining that the SIC value determined for the current period satisfies the trigger threshold.

Example 5. The method of any combination of examples 1-4, wherein triggering a confirmation test comprises triggering a lead impedance measurement test of a lead coupled to the medical device.

Example 6. The method of any combination of examples 1-5, wherein triggering a confirmation test comprises determining at least one of a geographic location of the medical device, a posture of a patient with the medical device, or an activity of the patient.

Example 7. The method of any combination of examples 1-6, wherein triggering a confirmation test comprises storing a cardiac electrogram at a computer readable storage location operatively coupled to the processing circuitry in response to determining that the SIC value determined for the current period satisfies the trigger threshold.

Example 8. The method of any combination of examples 1-7, wherein determining that a SIC value determined for the current period satisfies the trigger threshold comprises determining that the SIC value determined for the current period satisfies the trigger threshold prior to an end of the current period.

Example 9. The method of any combination of examples 1-8, wherein each respective period is one day.

Example 10. The method of any combination of examples 1-9, wherein the trigger threshold comprises the calculated measure of central tendency plus a constant.

Example 11. A medical device system, the system comprising: a medical device; and processing circuitry configured to: buffer a predetermined number of sensing integrity counter (SIC) values for the medical device, each of the buffered SIC values determined for a respective period of a plurality of periods preceding a current period; calculate a measure of central tendency for the buffered SIC values; determine a trigger threshold based on the calculated measure of central tendency; and trigger a sensing integrity alert in response to determining that a SIC value for the current period satisfies the trigger threshold.

Example 12. The system of example 15, wherein the measure of central tendency comprises any one of an average, a mode, or a median of the buffered SIC values.

Example 13. The system of any combination of examples 11-12, the predetermined number of SIC values is thirteen.

Example 14. The system of any combination of examples 11-13, the processing circuitry is further configured to trigger a confirmation test in response to determining that the SIC value determined for the current period satisfies the trigger threshold.

Example 15. The system of any combination of examples 11-14, wherein to trigger a confirmation test comprises triggering a lead impedance measurement test.

Example 16. The system of any combination of examples 11-15, wherein to trigger a confirmation test comprises determining a geographic location of the medical device, determining a posture of a patient with the medical device, or determining an activity of a patient with the medical device.

Example 17. The system of any combination of examples 11-16, wherein triggering a confirmation test comprises storing a cardiac electrogram at a computer readable storage location operatively coupled to the processing circuitry.

Example 18. The system of any combination of examples 11-17, wherein determining that a SIC value determined for the current period satisfies the trigger threshold comprises determining that the SIC value determined for the current period satisfies the trigger threshold prior to an end of the current period.

Example 19. The system of any combination of examples 11-18, wherein each respective period is one day.

Example 20. The system of any combination of examples 11-19, wherein the trigger threshold comprises the calculated measure of central tendency plus a constant.

Example 21. The system of any combination of examples 11-20, wherein the trigger threshold comprises a percentage increase greater than the calculated measure of central tendency.

Example 22. The system of any combination of examples 11-21, wherein the medical device comprises the processing circuitry.

Example 23. The system of any combination of examples 11-22, further comprising an external device configured to communicate with the medical device and comprising the processing circuitry.

Example 24. The system of any combination of examples 11-23, wherein the medical device is configured to be implanted in a patient.

Example 25. The system of any combination of examples 11-24, wherein the medical device is configured to be coupled to one or more leads, wherein each of the one or more leads comprise at least one electrode.

Example 26. A computer-readable medium comprising instructions for causing programmable processor processing circuitry to: buffer a predetermined number of sensing integrity counter (SIC) values for a medical device, each of the buffered SIC values determined for a respective period of a plurality of periods preceding a current period; calculate a measure of central tendency for the buffered SIC values; determine a trigger threshold based on the calculated measure of central tendency; and in response to determining that a SIC value for the current period satisfies the trigger threshold trigger a sensing integrity alert.

Various examples of the disclosure have been described. These and other examples are within the scope of the following claims.

What is claimed is:

1. A method comprising:
receiving, by processing circuitry of a medical device system comprising an implantable medical device including circuitry configured to sense a cardiac signal of a patient, indications of sensed heartbeats of the patient based on the sensed cardiac signal,
calculating, by the processing circuitry, intervals between adjacent heartbeats of the sensed heartbeats based on the indications;
incrementing, by the processing circuitry, a sensing integrity counter (SIC) based at least in part on the calculated intervals satisfying a predetermined interval threshold;
buffering SIC values for each respective period of time of a plurality of periods of time preceding a current period of time;
calculating, by the processing circuitry, a measure of central tendency of SIC values per period for the plurality of periods of time;
determining, by the processing circuitry, a trigger threshold for the current period of time based on the calculated measure of central tendency of SIC values per period; and
triggering a sensing integrity alert in response to determining that a SIC value determined for the current period of time satisfies the trigger threshold.

2. The method of claim 1, wherein the measure of central tendency comprises any one of an average, a mode, or a median of the buffered SIC values per period of time.

3. The method of claim 1, further comprising triggering a confirmation test in response to determining that the SIC value determined for the current period satisfies the trigger threshold.

4. The method of claim 3, wherein triggering a confirmation test comprises triggering a lead impedance measurement test of a lead coupled to the medical device.

5. The method of claim 3, wherein triggering a confirmation test comprises determining at least one of a geographic location of the medical device, a posture of a patient with the medical device, or an activity of the patient.

6. The method of claim 3, wherein triggering a confirmation test comprises storing a cardiac electrogram at a computer readable storage location operatively coupled to the processing circuitry in response to determining that the SIC value determined for the current period satisfies the trigger threshold.

7. The method of claim 1, wherein determining that a SIC value determined for the current period satisfies the trigger threshold comprises determining that the SIC value determined for the current period satisfies the trigger threshold prior to an end of the current period.

8. A medical device system, the system comprising:
a medical device; and
processing circuitry configured to:
receive an indication of sensed heartbeats of a patient based on a received sensed cardiac signal from the patient,
calculate an interval between sensed heartbeats based on the sensed cardiac signal;
increment a sensing integrity counter (SIC) based at least in part on the calculated interval satisfying a predetermined interval threshold;
buffer SIC values for each respective period of time of a plurality of periods of time preceding a current period of time;
calculate a measure of central tendency of SIC values per period for the plurality of periods if time;
determine a trigger threshold for the current period of time based on the calculated measure of central tendency of SIC values per period; and
trigger a sensing integrity alert in response to determining that a SIC value for the current period of time satisfies the trigger threshold.

9. The system of claim 8, wherein the measure of central tendency comprises any one of an average, a mode, or a median of the buffered SIC values per period of time.

10. The system of claim 8, wherein the processing circuitry is further configured to trigger a confirmation test in response to determining that the SIC value determined for the current period satisfies the trigger threshold.

11. The system of claim 10, wherein to trigger a confirmation test comprises triggering a lead impedance measurement test.

12. The system of claim 10, wherein to trigger a confirmation test comprises determining a geographic location of the medical device, determining a posture of a patient with the medical device, or determining an activity of a patient with the medical device.

13. The system of claim 10, wherein triggering a confirmation test comprises storing a cardiac electrogram at a computer readable storage location operatively coupled to the processing circuitry.

14. The system of claim 8, wherein determining that a SIC value determined for the current period satisfies the trigger threshold comprises determining that the SIC value determined for the current period satisfies the trigger threshold prior to an end of the current period.

15. The system of claim 8, wherein each respective period is one day.

16. The system of claim 8, wherein the trigger threshold comprises the calculated measure of central tendency plus a constant.

17. The system of claim 8, wherein the trigger threshold comprises a percentage increase greater than the calculated measure of central tendency.

18. The system of claim 8, wherein the medical device comprises the processing circuitry.

19. The system of claim 8, further comprising an external device configured to communicate with the medical device and comprising the processing circuitry.

20. A computer-readable medium comprising instructions for causing programmable processor processing circuitry to:
- receive an indication of sensed heartbeats of a patient based on received a sensed cardiac signal from the patient,
- calculate an interval between sensed heartbeats based on the sensed cardiac signals;
- increment a sensing integrity counter (SIC) based at least in part on the calculated interval satisfying a predetermined interval threshold;
- buffer SIC values for each respective period of time of a plurality of periods of time preceding a current period of time;
- calculate a measure of central tendency of SIC values per period for the plurality of periods of time;
- determine a trigger threshold for the current period of time based on the calculated measure of central tendency of SIC values per period; and
- in response to determining that a SIC value for the current period of time satisfies the trigger threshold trigger a sensing integrity alert.

* * * * *